(12) United States Patent
Kwon et al.

(10) Patent No.: US 8,637,103 B2
(45) Date of Patent: Jan. 28, 2014

(54) PRODUCTION OF ISOMALTOOLIGOSACCHARIDES AND USES THEREFOR

(75) Inventors: Hyuk-kon Kwon, Icheon (KR); Hea-seok Jeong, Icheon (KR); Jae-Ho Lee, Icheon (KR)

(73) Assignee: Corn Products Development, Inc., Westchester, IL (US)

( * ) Notice: Subject to any disclaimer, the term of this patent is extended or adjusted under 35 U.S.C. 154(b) by 9 days.

(21) Appl. No.: 13/214,787

(22) Filed: Aug. 22, 2011

(65) Prior Publication Data

US 2012/0052156 A1   Mar. 1, 2012

Related U.S. Application Data

(60) Provisional application No. 61/376,545, filed on Aug. 24, 2010.

(51) Int. Cl.
*A23L 1/08*     (2006.01)
*A23C 9/20*    (2006.01)

(52) U.S. Cl.
USPC .............................................. 426/48; 426/71

(58) Field of Classification Search
None
See application file for complete search history.

(56) References Cited

U.S. PATENT DOCUMENTS

| | | | |
|---|---|---|---|
| 4,113,509 A | 9/1978 | Leach et al. | |
| 5,763,385 A | 6/1998 | Bott et al. | |
| 5,824,532 A | 10/1998 | Barnett et al. | |
| 5,958,739 A | 9/1999 | Mitchinson et al. | |
| 6,008,026 A | 12/1999 | Day | |
| 6,303,346 B1 | 10/2001 | Liaw et al. | |
| 7,638,151 B2 * | 12/2009 | Duan et al. | 426/20 |
| 2005/0031734 A1 | 2/2005 | Duan et al. | |
| 2005/0153015 A1 * | 7/2005 | Inoue et al. | 426/18 |

FOREIGN PATENT DOCUMENTS

| | | |
|---|---|---|
| EP | 0875585 A1 | 11/1998 |
| WO | WO2004/081022 A2 | 9/2004 |

OTHER PUBLICATIONS

Shuren, Jin. "Production and use of modified starch and starch derivatives in China." Proc. 6th Regional Workshop, held in Ho Chi Minh city, Vietnam., Feb. 21-25, 2000, IAS CIAT:559-560. http://webapp.ciat.cgiar.org/asia_cassava/pdf/proceedings_workshop_00/553.pdf, accessed Nov. 21, 2012.*

Lucia Fernandez-Arrojoa, Dolores Marin , et al. Transformation of maltose into prebiotic oligosaccharides by a novel alpha-glucosidase from Xantophyllomyces dendrorhous. Process Biochemistry 42 (2007) 1530-1536.*

Enzymes in Food Technology Second Edition—Chapter 14. Starch-Processing Enzymes Robert J. Whitehurst, Maarten van Oort Marc J. E. C. van der Maarel1 ,Published Online: Sep. 22, 2009 DOI: 10.1002/9781444309935.ch14 Copyright © 2010 Blackwell Publishing Ltd, Figure 14.4, p. 323.*

Schulein, et al. Characterization of a New Class of Thermophilic Pullulanases From *Bacilus acidopullulyticus*, Annals of the New York Academy of Sciences, vol. 434, Issue 1, pp. 271-274 (1984).

* cited by examiner

*Primary Examiner* — Humera Sheikh
*Assistant Examiner* — Subbalakshmi Prakash
(74) *Attorney, Agent, or Firm* — Foley & Lardner LLP

(57) ABSTRACT

Described herein are methods for preparing isomaltooligosaccharides ("IMOs") from a carbohydrate substrate and uses thereof. In the presence of a maltogenic enzyme and additional IMO precursors, an *Aspergillus* sp. invertase is capable of producing IMOs from a starch slurry. The ability of the invertase to function as a transglucosidase enzyme imparts a simultaneous mechanism for IMO saccharification.

16 Claims, 2 Drawing Sheets

PRODUCTION OF ISOMALTOOLIGOSACCHARIDES AND USES THEREFOR

CROSS REFERENCE TO RELATED APPLICATIONS

This application claims priority to U.S. Provisional Application No. 61/376,545 filed Aug. 24, 2010, the entire contents of which is incorporated herein by reference in its entirety.

TECHNICAL FIELD

The present technology generally relates to methods for producing isomaltooligosaccharides with invertase derived from *Aspergillus niger* and/or *Aspergillus oryzae* and uses thereof. The methods produce isomaltooligosaccharides from a carbohydrate substrate.

BACKGROUND

The following description is provided to assist the understanding of the reader. None of the information provided or references cited is admitted to be prior art.

Isomaltooligosaccharides ("IMO" or "IMOs") are mixed linkage oligosaccharides, having mixtures of α-(1,4)- and/or α-(1,6)-glucosidic linkages. IMOs include isomaltose, panose, isomaltotriose, isomaltotetraose, isopanose, and other higher branched oligosaccharides, such as, fructooligosaccharides, galactooligosaccharides, xylooligosaccharides, and gentiooligosaccharides. IMO production occurs via a complex enzymatic process, whereby a starting raw material is converted to a maltose substrate, e.g., corn syrup. Subsequently, IMOs are synthesized by an enzyme-catalyzed transglucosidic reaction.

IMOs belong to a group of oligosaccharides classified as functional-health food oligosaccharides ("FHFO"). IMOs have been linked to an increase in health when consumed on a regular basis, and are sometimes referred to as "prebiotics." Prebiotics are defined as non-digestible substances, e.g., dietary fiber, that exert some biological effect on an individual via stimulating the growth of commensal or beneficial microorganisms. IMOs can be used as a sweetening product that may be used in foods and beverages.

SUMMARY

In one aspect, the present disclosure provides a method for making an isomaltooligosaccharide composition comprising: (a) contacting a starch slurry with a liquefaction enzyme; and (b) contacting the product of (a) with a maltogenic enzyme and an invertase, wherein the maltogenic enzyme and the invertase are contacted separately, sequentially, or simultaneously to produce isomaltooligosaccharides.

In one embodiment, the maltogenic enzyme and the invertase are contacted simultaneously. In one embodiment, the slurry comprises 15% to 45% by weight of starch. In one embodiment, the invertase is at least 0.0009% by weight of all reactants of (b). In one embodiment, the invertase is less than 2% by weight of all reactants of (b). In one embodiment, (b) occurs at a pH above 2 and below 10. In one embodiment, (b) occurs at a temperature above 10° C. and below 85° C.

In one aspect, the isomaltooligosaccharides are selected from the group consisting of isomaltose, branched glucose, DP3 glucose, panose, isomaltotriose, isomaltotetraose, isomaltopentaose, isomaltohexaose, and isomaltoheptose, or any combination thereof. In one embodiment, at least 10% of the produced isomaltooligosaccharides is panose. In one embodiment, the method further comprises purifying the isomaltooligosaccharides.

In one embodiment, the liquefaction enzyme is an alpha-amylase. In one embodiment, the maltogenic enzyme is a beta-amylase. In one embodiment, the invertase has transglucosidase activity. In one embodiment, the invertase is an *Aspergillus* invertase. In one embodiment, the *Aspergillus* invertase is an *Aspergillus niger* invertase. Additionally or alternatively, in some embodiments, the *Aspergillus* invertase is an *Aspergillus oryza* invertase.

In one embodiment, the slurry is formed from one or more starch and liquid. In one embodiment, the one or more starch is selected from the group consisting of corn starch, rice starch, wheat starch, tapioca, potato starch, sweet potato starch, sago starch, barley starch, heat/acid treated starch, pearl starch, waxy corn starch, sorghum starch, high amylase corn starch, liquid dextrose, and combinations thereof. In one embodiment, the starch is corn starch.

In one aspect, an isomaltooligosaccharide composition is produced by a method for making an isomaltooligosaccharide composition comprising: (a) contacting a starch slurry with a liquefaction enzyme; and (b) contacting the product of (a) with a maltogenic enzyme and an invertase, wherein the maltogenic enzyme and the invertase are contacted separately, sequentially, or simultaneously.

In one aspect, a food additive comprising isomaltooligosaccharides is produced by a method for making an isomaltooligosaccharide composition comprising: (a) contacting a starch slurry with a liquefaction enzyme; and (b) contacting the product of (a) with a maltogenic enzyme and an invertase, wherein the maltogenic enzyme and the invertase are contacted separately, sequentially, or simultaneously.

In one aspect, a food product comprising at least one food ingredient and isomaltooligosaccharides is produced by a method for making an isomaltooligosaccharide composition comprising: (a) contacting a starch slurry with a liquefaction enzyme; and (b) contacting the product of (a) with a maltogenic enzyme and an invertase, wherein the maltogenic enzyme and the invertase are contacted separately, sequentially, or simultaneously.

DETAILED DESCRIPTION

Figure 1:
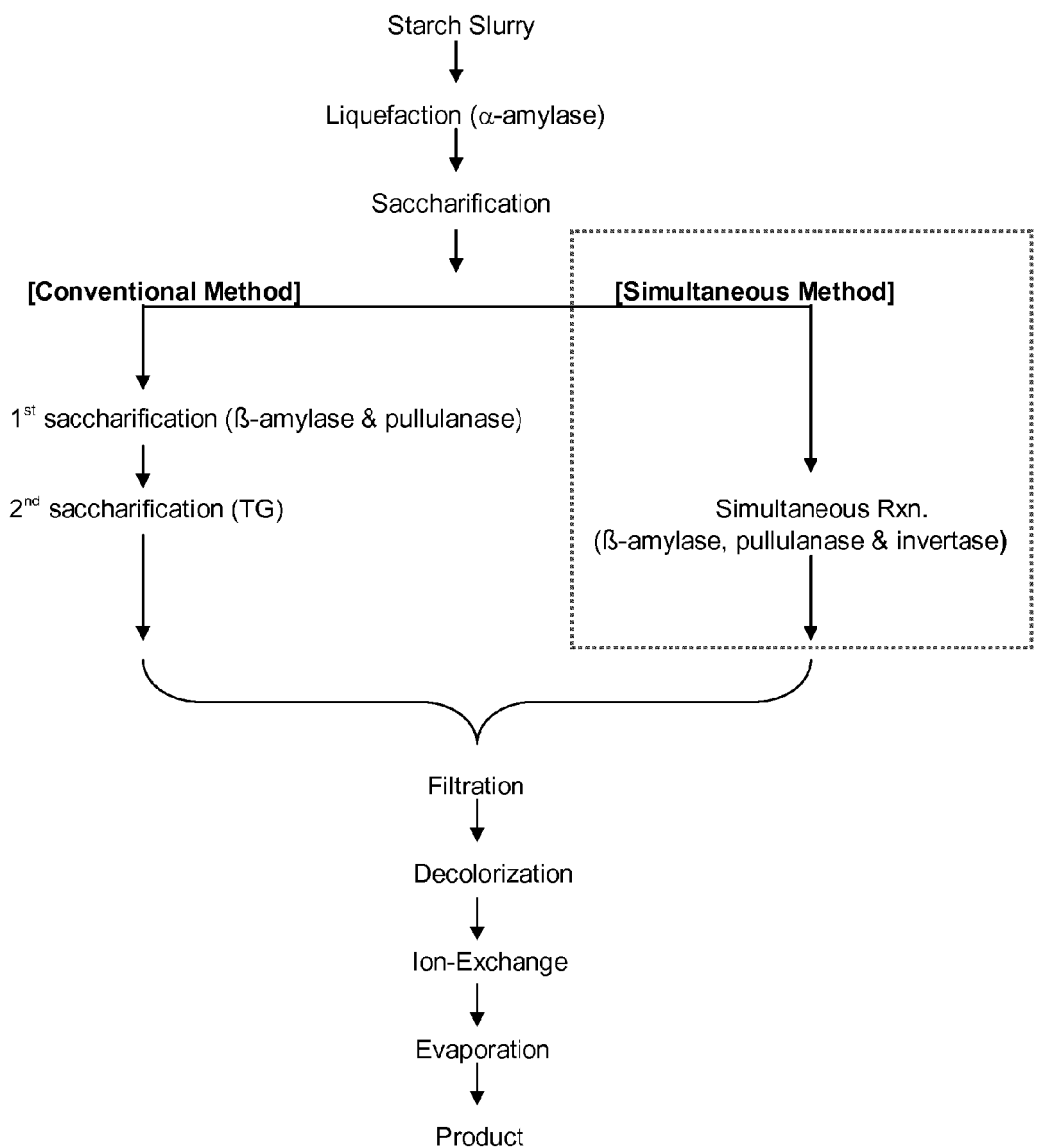
FIG. 1 is a chart depicting the conventional and simultaneous saccharification reactions.

Disclosed herein are methods for producing oligosaccharides, particularly IMOs. Further disclosed herein are methods, steps, and reactions for the commercial production of IMOs using steps which impart an improved method for expedient IMO manufacturing.

In the following detailed description, the illustrative embodiments described in the detailed description, figures, and claims are not meant to be limiting. Other embodiments may be utilized, and other changes may be made, without departing from the spirit or scope of the subject matter presented here. In the description that follows, a number of terms are used extensively. The terms described below are more fully understood by reference to the specification as a whole. Units, prefixes, and symbols may be denoted in their accepted SI form.

The terms "a" and "an" as used herein mean "one or more" unless the singular is expressly specified. Thus, for example, reference to "a carbohydrate" includes a mixture of two or more carbohydrates, as well as a single carbohydrate.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to, plus or minus 10% of the particular term.

As used herein, the term "carbohydrates" will be understood by one skilled in the art to include polyhydroxy-aldehydes or -ketones and compounds derived therefrom. Carbohydrates can include compounds composed of at least one basic monosaccharide unit. They may be classified as simple carbohydrates and complex carbohydrates. Simple carbohydrates are monosaccharides and disaccharides. Complex carbohydrates are polysaccharides, or large molecules composed of straight or branched chains of monosaccharides.

As used herein, the term "liquefaction syrup" or "liquefying syrup" refers to a carbohydrate substrate, e.g., starch, that has been reacted with a liquefaction enzyme, such as, but not limited to, an α-amylase. A liquefaction syrup is produced via a liquefaction reaction.

As used herein, the term "liquefaction reaction" refers to an enzymatic or chemical reaction that reduces the viscosity and/or increases the fluidity of one or more carbohydrates in a mixture.

As used herein, the term "transglucosidic" or "transglucosidase", refers to the enzyme or activity that catalyzes hydrolytic and/or transfer reactions to form new α-1,6 linkages. These enzymes include, but are not limited to, transglucosidases and invertases.

As used herein, the term "liquefaction enzyme" or "liquefying enzyme" can be one of many α-amylases or other amylases. Liquefaction enzymes effect the fluidity or viscosity of starch, i.e., starch fluidization. Exemplary starch liquefying enzymes include α-amylases.

As used herein, a "maltogenic enzyme" refers to an enzyme that catalyzes the production of maltose from a larger carbohydrate polymer. A maltogenic enzyme can be one of many β-amylases or other amylases. A maltogenic reaction produces maltose.

As used herein, the term "invertase" or "invertases" refers to a class of enzymes that catalyzes hydrolytic and transfer reactions to form new α-1,6 linkages. Invertases catalyze the synthesis of sugars by transferring monosaccharides via a transglycosylation reaction. For example, an invertase useful in the present methods possesses transglucosidase activity, i.e., it catalyzes the hydrolysis of saccharides by hydrolyzing glycosidic linkages. An invertase can be a plant, animal, bacterial, or fungal invertase. In one embodiment, the invertase is an *Aspergillus* sp. invertase. By way of example, but not by way of limitation, in some embodiments, invertases are derived from *Aspergillus niger* and/or *Aspergillus oryza*. As used herein, "an invertase with transglucosidase activity" or "an invertase of the present technology" refers to an invertase that is capable of catalyzing a saccharification reaction.

As used herein, a "saccharification reaction" or "saccharification" refers to the process of converting a liquefaction syrup to IMOs via maltogenic and transglucosidic reactions. The saccharification reactions described herein can occur in one or more steps or reactions, wherein the steps or reactions occur separately, sequentially, or simultaneously.

Methods of IMO Production

The present technology encompasses an improved method for IMO production. The improved method of IMO production occurs when a carbohydrate substrate is reacted with a liquefaction enzyme, in addition to separate, sequential, or simultaneous saccharification reactions, to produce an IMO product.

In one aspect, the present technology provides a method for making an isomaltooligosaccharide composition comprising the steps of: (a) contacting a starch slurry with a liquefaction enzyme; and (b) contacting the product of step (a) with a maltogenic enzyme and an invertase, wherein the maltogenic enzyme and the invertase are contacted separately, sequentially, or simultaneously to produce isomaltooligosaccharides.

In some embodiments, the methods herein include a first saccharification reaction and a second saccharification reaction, or a simultaneous saccharification reaction. In one embodiment, the first saccharification reaction results in the production of a maltogenic product, i.e., maltose or a maltose syrup. The second saccharification reaction includes applying one or more enzymes, such as invertase with transglucosidic activity, to the maltogenic product, whereby some or all of the maltogenic product is converted to IMOs. In one embodiment, the conversion of the raw material, i.e., starch slurry, to maltose occurs during a first saccharification reaction, i.e. a maltogenic reaction. The production of IMO occurs during a second saccharification reaction, i.e., the transglucosidic reaction, wherein invertase with transglucosidic activity is employed during the reaction.

Substrates

The present methods use a carbohydrate substrate. As described herein, the term "carbohydrate" or "carbohydrate substrate" refers to, but is not limited to, starch, natural unmodified starch, corn starch, wheat starch, tapioca starch, potato starch, sweet potato starch, sago starch, barley starch, rice starch, heat/acid treated starch (dextrin), pearl starch, waxy corn starch, sorghum starch, high amylose corn starch, liquid dextrose of high solid content, and combinations thereof.

In one embodiment, the carbohydrate substrate is a starch substrate. The starch substrate can be, but is not limited to, corn starch. In one embodiment, the carbohydrate substrate is a starch slurry. As described herein, the term "slurry" refers to an aqueous mixture containing insoluble components such as, but not limited to, starch granules. Sometimes the terms "slurry" or "syrup" or "suspension" are used interchangeably herein. As described herein, the term "starch substrate" or "starch slurry" refers to a liquid solution in combination with a starch, wherein a starch is any material composed of the complex polysaccharide carbohydrates with the formula $(C_6H_{10}O_5)x$, wherein X can be any number. The liquid can be any aqueous solvent, e.g., water.

In one embodiment, the starch slurry includes one or more various forms of starch. As described in U.S. Pat. No. 7,638, 151, one form of starch is, amylose, a linear chain polysaccharide. Other forms of starch include amylopectin, a branched chain polysaccharide. Amylose contains long unbranched chains in which all the D-glucose units are linked by α-(1,4)-linkages, i.e., "α-(1,4)-linkages" or "1,4-α-D-glucosyl linkages". Amylopectin is highly branched, where the backbone glucosidic linkages are α-(1,4)-linkages, however, the branch points also provide for α-(1,6)-linkages. As used herein, the term "linkage" or "linkages" refers to the number of the carbon moiety to which a glucose or other molecule is attached. The α (alpha) and β (beta) prefixes denote whether the linkage is axial or equatorial to the carbon ring, respectively. Accordingly, alpha linkages are equatorial to the ring and beta linkages are axial.

In one embodiment, the amount or concentration of starch substrate, i.e., the concentration of the starch slurry, can be an aqueous slurry having a concentration between 1-60%, 5-45%, 10-40%, 20-40%, or 25-35% dissolvable solids ("ds"). As described herein, the term "dissolvable solids" or "ds" refers to the percentage of solid, i.e., starch, that is suspended in solution. In one embodiment, the pH of the slurry is between 1.0-9.0, 2.0-8.0, 3.0-7.5, 4.0-6.5, or 4.5-6.0. In another embodiment, the pH of the slurry is between 5.8-6.1. In one aspect, the present technology provides for the concentration or density of a starch slurry between 5-25, 10-25, 15-23, or 18-22° Be. In one embodiment, the density of the slurry is between 19-22° Be. As used herein, "° Be" or "Baum" density is measured as a function of the specific gravity of a starch slurry at a specific temperature.

Liquefaction Reaction

In one embodiment, the starch slurry is contacted with a liquefying enzyme, thereby producing a liquefaction syrup. In one embodiment, liquefaction may include the enzymatic hydrolysis of the major components of starch. In one embodiment, amylose can be hydrolyzed by an α-amylases, e.g., α-(1,4)-glucan 4-glucanohydrolase. The α-amylases hydrolyze α-(1,4)-linkages to yield a mixture of glucose, maltose, maltotriose and higher sugars. See e.g., U.S. Pat. No. 4,113,509. Amylose may also be hydrolyzed by a β-amylase. β-amylases cleave successive maltose units beginning from the non-reducing end to quantitatively yield maltose. The α- and β-amylases also hydrolyze amylopectin. Neither the α- nor β-amylases can hydrolyze the α-(1,6)-linkages at the branch points of amylopectin. The end product of exhaustive β-amylase action on amylopectin is a large, highly branched core or β-limit dextrin. A debranching enzyme, e.g., pullulanases, α-(1,6)-glucan-6-glucanohydrolase, or α-(1,6)-glucosidase, can hydrolyze the α-(1,6)-linkages at the branch points. As used herein, the term "debranching enzyme" refers to enzymes that catalyze the hydrolysis of α-(1,6)-linkages. An exemplary debranching enzyme is a pullulanase, also known as α-dextrin-endo-(1,6)-α-glucosidase, limit dextrinase, debranching enzyme, or (1,6)-glucanohydrolase, See e.g., Schüllein, et al., *Characterization of a New Class of Thermophilic Pullulanases from Bacillus acidopullulyticus*, Annals of the New York Academy of Sciences, Vol. 434, Issue 1, pp. 271-74 (2006).

In one aspect, the liquefying enzyme is an enzyme derived, isolated, or extracted from a bacterial, fungal, plant, or other source. In one embodiment, the bacterial source is a *Bacillus* sp. α-amylase. In one embodiment, the α-amylase is derived from a *Bacillus* sp. including those derived from at least one bacterial source selected from *B. subtilis*, *B. licheniformis*, *B. stearothermophilus*, *B. coagulans*, *B. amyloliquefaciens*, and *B. lentus*. In one embodiment, an α-amylase from *B. licheniformis* or *B. stearothermophilus* is the liquefaction enzyme. In another embodiment, amylases other than α-amylase are used as a liquefaction enzyme. In one embodiment, amylases characterized by increased oxidation or thermostability, including mutants, genetically modified amylases, or variant amylases as described in U.S. Pat. Nos. 5,763,385, 5,824,532, 5,958,739, and 6,008,026, are contemplated. In one embodiment, the liquefying enzyme is a heat stable α-amylase.

In one embodiment, the liquefying enzyme is contacted with a starch slurry to reduce the viscosity of the liquefied or solubilized starch. The insoluble starch components are converted to soluble material via dextrinization. As used herein, the term "dextrinization" refers to the conversion of starch to soluble polysaccharides or oligosaccharides. In one embodiment, one or more liquefying enzymes are added to a starch slurry. The liquefying enzyme may be added to the slurry manually or automatically, in the amounts of 0.0001-10%, 0.001-5%, or 0.01-1% (w/w/ds). In one embodiment, the liquefying enzyme may be added to the slurry in the amounts of 0.40-0.70%, 0.50-0.60%, or 0.55% (w/w/ds). In one embodiment, the liquefying enzyme may be added to the slurry in the amounts of 0.55% (w/w/ds).

In one embodiment liquefaction enzyme concentrations are between 0.0001-10%, 0.001-5%, or 0.005-1% (w/w/ds) of liquefying enzyme to ds of starch slurry. In one embodiment, liquefaction enzyme concentrations are between 0.015-0.035% or 0.022-0.025% (w/w/ds) of liquefying enzyme to ds of starch slurry. In another embodiment, liquefaction enzyme concentrations between 0.04-0.07%, 0.05-0.06%, or 0.04-0.05% (w/w/ds) are employed. In one embodiment, the liquefaction enzyme concentration is 0.045% (w/w/ds) of liquefying enzyme to ds starch slurry.

In one embodiment, a liquefying enzyme is reacted with a starch slurry for 15-210 minutes ("min"), 60-210 min, 90-180 min, or 120-150 min, at a suitable temperature. In one embodiment, a liquefying enzyme is reacted with a starch slurry for about 130 min at a suitable temperature. The liquefying enzyme may be added to the slurry manually or automatically, at temperatures between 90-125° C., 95-115° C., 100-110° C., or 100-108° C. In one embodiment, the pH of the liquefaction reaction is maintained at a range between 4.0-8.0, 5.0-7.0, or 5.8-6.1. A skilled artisan will recognize that the pH of the liquefaction reaction can be maintained through the use and application of suitable amounts of an acid or a base, e.g., hydrochloric acid ("HCl") or sodium hydroxide ("NaOH"), when necessary. In one embodiment, a liquefaction syrup containing IMO precursors is produced via a liquefaction reaction.

Maltogenic Reaction

In one embodiment, a starch slurry is contacted with a liquefying enzyme and then a maltogenic enzyme, thereby producing maltose. In one embodiment, a starch slurry is contacted with a liquefying enzyme containing maltogenic enzymatic functionalities, thereby producing a liquefaction syrup containing maltose. As used herein, the term "maltogenic enzyme" refers to an enzyme that converts carbohydrates to maltose and derivatives thereof. Exemplary maltogenic enzymes include, but are not limited to, fungal, bacterial, and plant derived α-amylases and β-amylases. The term "maltose", as used herein, refers to a disaccharide having two glucosyl residues linked by an α-(1,4)-D-glucosidic linkage. In one embodiment, the maltose is produced from a maltose rich slurry or syrup, i.e., a liquefaction syrup.

In some embodiments, saccharification reactions include the hydrolysis of liquefied carbohydrate substrates, i.e., the liquefaction syrup. The saccharification reactions include a maltogenic reaction and a transglucosidic reaction, wherein the reactions can occur separately, sequentially, or simultaneously. The saccharification reactions are generally performed by adding one or more saccharification enzymes to the liquefaction syrup. In one embodiment, one or more enzymes selected from the group of β-amylase, transglucosidase, invertase, pullulanase, and combinations thereof, are reacted with the liquefaction syrup to produce IMOs or IMO precursors. As used herein, "IMO precursors" refers to a composition containing any constituent component of an IMO that is required to form IMOs. In one embodiment, an IMO precursor is maltose or derivatives thereof.

In some embodiments, hydrolysis of a liquefaction syrup occurs in the presence of a maltogenic enzyme. In one embodiment, the maltogenic enzyme is a β-amylase. While some α-amylases are maltogenic to the extent that contacting α-amylases with a starch substrate can produce maltose, the use of β-amylases are beneficial in that their contact with various starches provide for an increased amount of IMO precursors, i.e., maltose, to the exclusion of other saccharides, such as glucose, See e.g., U.S. Pat. Nos. 4,970,158 and 4,647,538. In one embodiment, the β-amylase is a plant, microbial enzyme, or a thermostable bacterial, β-amylase. It will be readily understood by the skilled artisan that suitable β-amylase may be naturally-occurring as well as recombinant and mutant β-amylases. As used herein, the term "β-amylase" refers to enzymes that catalyze the hydrolysis of α-(1,4)-glucosidic linkages, thereby releasing maltose units. β-amylase have also been described as enzymes effecting the hydrolysis of (1,4)-α-D-glucosidic linkages in polysaccharides as to remove successive maltose units from the non-reducing end of saccharide chains, See e.g., U.S. Pat. No. 7,638,151.

In one embodiment, the maltogenic reaction is conducted for at least 12, 20, 72, or 120 hours ("h"). In one embodiment, a maltogenic reaction is performed at temperatures ranging from 40° C., 50° C., 55° C., 60° C., and 65° C., to 90° C. In one embodiment, the maltogenic reaction occurs at a temperature between 60-65° C. In one embodiment, a maltogenic reaction occurs at an alkaline pH between 4.0-, 5.0-, 5.5-, 6.0-, and 7.0. In one embodiment, the pH of the maltogenic reacting is between 5.0-5.5. A skilled artisan will recognize that the pH of the maltogenic reaction can be maintained through the use and application of suitable amounts of an acid or a base, e.g., hydrochloric acid ("HCl") or sodium hydroxide ("NaOH"), when necessary.

In some embodiments, the present methods include a suitable amount of maltogenic enzyme applied during a maltogenic reaction as a function of the amount of dissolved maltose present in a liquefaction syrup. To this end, after liquefaction of the carbohydrate, i.e., starch, the dissolved maltose content of the liquefaction syrup is determined and a suitable amount of maltogenic enzyme is applied to a maltogenic reaction. The amount of maltogenic enzyme ranges from 0.0001-10% (w/w), or from 0.0005-1% (w/w), or from 0.001% to 0.25% (w/w) depending on the specific maltogenic enzyme to be added, and the total weight of the liquefaction syrup, i.e., the solid content of the syrup.

In one embodiment, between 0.0001-10% (w/w) pullulanase is applied to a saccharification reaction during the maltogenic reaction. In one embodiment, between 0.001-1% (w/w) pullulanase is applied to a saccharification reaction during the maltogenic reaction In another embodiment, 0.05-0.1% (w/w) pullulanase is applied to a saccharification reaction during the maltogenic reaction.

In one embodiment, a maltogenic enzyme and/or pullulanase may be added to a first saccharification or a maltogenic reaction at a concentration between 0.001-1% (w/w) at a Brix relative density between 35-40° Bx. As described herein, the term "Brix relative density", "Brix", or "° Bx", refers to a well known hydrometer scale for measuring the sugar content of a solution at a given temperature. Thus, the unit ° Bx, refers to a measure of the solubilized sugars in solution. The Brix scale measures the number of grams of sugar present per 100 grams of aqueous sugar solution (the total solubilized solid content). For example, a measurement of 1.0° Bx refers to 10 mg/ml of sugar in solution. In one embodiment, between 0.01-0.1% (w/w) of maltogenic enzyme and/or pullulanase is applied to a 35-40° Bx first saccharification reaction or a maltogenic reaction. In one embodiment, β-amylase is a maltogenic enzyme applied to the first saccharification reaction. In one embodiment, both β-amylase and pullulanase are applied to a first saccharification reaction.

In one embodiment, β-amylase is applied to a 35-40° Bx first saccharification reaction or a maltogenic reaction, in the presence or absence of pullulanase, at a concentration between 0.005-5%, 0.01-1%, or 0.02-0.05% (w/w). In another embodiment, pullulanase is applied to a 35-40° Bx first saccharification reaction or a maltogenic reaction, at a concentration between 0.005-5%, 0.01-1%, or 0.02-0.05% (w/w). In one embodiment, pullulanase is applied to a 35-40° Bx first saccharification reaction or a maltogenic reaction, at a concentration of 0.025% (w/w).

In some embodiments, the maltogenic reaction proceeds for 10-100 hours ("h"). In one embodiment, the maltogenic reaction proceeds for 15-30 h. In one embodiment, the maltogenic reaction proceeds for 20-24 h. In one embodiment, the maltogenic reaction occurs at a temperature between 50-70° C. In another embodiment, the maltogenic reaction occurs at a temperature between 55-65° C. In one embodiment, the maltogenic reaction occurs at an alkaline pH. In one embodiment, the pH of the maltogenic reaction is between 4.0-7.0. In another embodiment, the maltogenic reaction occurs at a pH between 5.5-5.8. A skilled artisan will recognize that the pH of the maltogenic reaction can be maintained through the use and application of suitable amounts of an acid or a base, e.g., hydrochloric acid ("HCl") or sodium hydroxide ("NaOH"), when necessary.

Transglucosidic Reaction

The transfer of glucose moieties, and derivatives thereof, can occur in the presence of a transglucosidic enzyme. The maltogenic reaction and transglucosidic reaction can occur separately, sequentially, or simultaneously, depending on the saccharification enzymes that are applied to a specific reaction. In one embodiment, a simultaneous saccharification reaction occurs in the presence of an invertase. In one embodiment, the simultaneous saccharification reaction includes the maltogenic reaction and the transglucosidic reaction. For example, transglucosidic reaction may occur concomitantly with the maltogenic reaction, thereby imparting a simultaneous saccharification reaction. As used herein, a "simultaneous saccharification reaction" refers to a first saccharification reaction and a second saccharification reaction that occur in temporal and spatial proximity. In a simultaneous saccharification reaction the product of the first saccharification reaction is immediately available for use as a substrate in a second saccharification reaction. In one embodiment, the simultaneous saccharification reaction occurs in the presence of a maltogenic enzyme and an invertase having transglucosidic activity. Another aspect of the present technology discloses an invertase that reacts with a maltogenic substrate. In one embodiment, an invertase with transglucosidic activity reacts with a maltogenic substrate.

In one embodiment, the transglucosidic reaction is performed sequentially by adding one or more saccharification enzymes to the product of the maltogenic reaction. In one embodiment, one or more enzymes are selected from the group of β-amylase, transglucosidase, invertase, pullulanase, and combinations thereof, are reacted with a liquefaction syrup or the product of the maltogenic reaction to produce IMOs during a transglucosidic reaction. In one embodiment, invertase is the transglucosidic enzyme reacted with the liquefaction syrup to produce IMOs during the transglucosidic reaction. In another embodiment, an *Aspergillus* sp. invertase is the transglucosidic enzyme reacted with the liquefaction syrup to produce IMOs during the transglucosidic reaction.

In another embodiment, the transglucosidic reaction is catalyzed by two or more enzymes. For example, a combination of an invertase with transglucosidase activity and a transglucosidase ("TG") may be used in the saccharification reaction. In one embodiment, the transglucosidic enzyme is an *Aspergillus* sp. TG. In one embodiment, the transglucosidic enzyme is an *Aspergillus niger* TG. While TG, as previously described herein, can function as a transglucosidase, the use of an invertase is beneficial in that its contact with various starch- and maltose-based substrates provide for increased IMO production when compared to conventional methods using TG.

In one embodiment, the transglucosidic reaction, i.e., the second saccharification reaction, is performed for 10-100 h. In one embodiment, the second saccharification reaction occurs for 30-90 h. In one embodiment, the second saccharification reaction occurs for 48-72 h. In one embodiment, the second saccharification reaction is heated for 10-100 h, 30-90 h, or 48-72 h at a temperature between 50-70° C. In another embodiment, the second saccharification reaction is heated for 10-100 h, 30-90 h, or 48-72 h at a temperature between 55-65° C. In one embodiment, the second saccharification reaction occurs at 60-65° C. In one embodiment, the reaction occurs at an alkaline pH between 4.0-, 5.0-, 5.5-, 6.0-, and 7.0. In one embodiment, the pH of the second saccharification reaction is between 5.0-5.5. A skilled artisan will recognize that the pH of the second saccharification reaction can be maintained through the use and application of suitable amounts of an acid or a base, e.g., hydrochloric acid ("HCl") or sodium hydroxide ("NaOH"), when necessary.

In some embodiments, a suitable amount of invertase is applied to a simultaneous saccharification reaction as a function of the amount of substrate in the liquefaction syrup. To this point, after liquefaction of the carbohydrate, i.e., starch, the dissolved maltose content of the syrup can be determined and a suitable amount of enzyme is applied for a simultaneous saccharification reaction. The amount of enzyme will vary depending on the total weight of the liquefaction syrup, i.e., the dry solid content. In addition to applying invertase, one or more maltogenic enzymes are also applied to the simultaneous saccharification reaction.

In one embodiment, between 0.0001-10% (w/w) invertase is applied as a saccharification enzyme to the saccharification reaction. In one embodiment, between 0.001-5% (w/w) invertase is applied as a saccharification enzyme to the saccharification reaction. In one embodiment, between 0.01-1% (w/w) invertase is applied to the saccharification reaction. In one embodiment, between 0.05-0.5% (w/w) invertase is applied to the saccharification reaction. In another embodiment, 0.16% (w/w) invertase is applied to the saccharification reaction.

Saccharification enzymes can be applied to a simultaneous saccharification reaction manually or automatically, either alone or in combination, at concentrations previously described, wherein the Brix density of the liquefaction syrup is between 35-40° Bx. In one embodiment, the Brix density of the liquefaction syrup is 36° Bx. In one aspect, the saccharification reaction converts some or all of the maltogenic product to IMOs.

IMO Purification and Uses Thereof

In some embodiments, the present methods include a step of removing foreign materials from the IMO reactions. Foreign materials include, but are not limited to, unreacted raw materials and denatured proteins, carbohydrates, and starch. In some embodiments, the purification includes, but is not limited to, filtration, sedimentation, and coagulation, including variations and combinations thereof. In one embodiment, IMO syrup is filtered using a filtration device. Filtration devices, which press and aid in filtration, include: drum filters; rotary drum filters; perlite; cellite; and combinations thereof.

In some embodiments, the methods include a decoloration step. Decoloration is achieved by treating the IMO products or IMO syrup with a material capable of removing color inducing material, such as granular active carbon. In one embodiment, the IMO syrup is passed over a carbon column that is charged with granular active carbon at a temperature between 60-90° C. or between 70-75° C. In one embodiment, the IMO syrup can be passed over a carbon column for 10 min-15 h at 36° Bx. In one embodiment, the IMO syrup can be passed over a carbon column for 1-15 h at 36° Bx. In another embodiment, the IMO syrup can be passed over a carbon column for 5-10 h at 36° Bx.

In some embodiments, the methods include separation of ionic components from the IMO syrup. A first means for separation capable of removing ionic species from the IMO syrup includes, but is not limited to, ion exchange resins, ultra-filtration, reverse osmosis, and other chromatographic techniques that will be readily known by a skilled artisan. In one embodiment, a first separation step is conducted at a temperature between 40-75° C. or between 55-60° C.

In one embodiment, the first means for separation further includes cationic exchange resins, anionic exchange resins, or combinations thereof. Suitable cationic resin volumes include 0.1-100% (v/v) or 1-5% (v/v) based on the volume of the IMO syrup. In one embodiment, anionic exchange resins may be used. Suitable anionic resin volumes include 0.1-100% (v/v) or 2-10% (v/v) based on the volume of the IMO syrup.

In one embodiment, ion exchange may be performed by passing IMO syrup over an ion exchange column. In one embodiment, the ion exchange column contains a cationic exchange resin, anionic exchange resin, or both. In one embodiment, the flow rate of the IMO syrup in the ion exchange column is between 0.1 ml/min to 1000 l/min or between 10-50 l/min.

In one embodiment, the IMO syrup is processed using separate exchange resins. To this end, the IMO syrup is first passed over a cationic exchange resin and subsequently passed over an anionic exchange resin. In one embodiment, the IMO syrup is additionally, or in the alternative, passed over a resin containing both cationic and anionic resin species. In one embodiment, a transportation pump is used to pass the IMO syrup over the exchange resins described herein. In one embodiment, ion exchange chromatography is performed at 40-75° C. In one embodiment, the ion exchange chromatography is performed at 55-60° C.

In some embodiments, the methods include concentrating the IMO syrup to a desired moisture or solids content. In one embodiment, the IMO syrup is concentrated to 30-75° Bx, 40-50° Bx, or 45-50° Bx. To this end, the IMO syrup is processed via a means for removing moisture to concentrate the IMO syrup. In one embodiment, a means for removing moisture is evaporation. In one embodiment, a continuous or non-continuous Mechanical Vapor Recompressor ("MVR") can be used. Other evaporation or vapor devices known in the art, such as a triple evaporator, can also be used and will be readily known to the skilled artisan.

In one embodiment, after the IMO syrup is concentrated, catalytic IMO hydrogenation is performed. In one embodiment, catalysts include platinum group metals, such as, platinum, palladium, rhodium, and ruthenium. Non-precious metal catalysts, such as, nickel, nickel alloy, Raney nickel, and Urushibara nickel can be used as catalysts for the present technology.

In one aspect, the present technology provides IMOs that are produced using the methods described herein. The methods may be used to produce various IMOs. In one embodiment, branched glucose, DP3 glucose, panose, isomaltotriose, isomaltotetraose, isomaltoheptose, or combinations thereof, are produced.

In one embodiment, the IMOs produced using the present methods can be employed as food additives or sweeteners. In one embodiment, by concentrating and drying the IMO syrup, slurry, separated insoluble components, and/or separated soluble components, a flour or other dried powder can be obtained therefrom. The resulting powder or flour can be incorporated into compositions in which the presence of IMOs is desired, for example in food stuffs, i.e., breakfast cereals, pastas, or food additives, and baked goods. As described herein, the term "food additive" or "food additives" refers to the use of an IMO or IMOs as a sprinkle-on material, as an ingredient for use in the manufacture of other foods, and/or a topical ingredient added to food and/or liquids.

In another embodiment, the dried powder can be incorporated into food supplements. The incorporation of the dried powder into a food supplement can be provided in any acceptable supplement or form. The dietary supplements can be formulated for oral administration in a matrix, e.g., drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension. The dietary supplement can also be formulated for oral administration as a solution or suspension in an aqueous liquid, as a liquid incorporated into a gel capsule or as any other convenient form for administration or for rectal administration, as a suppository, enema or other convenient form. The IMOs can also be provided as a controlled release system.

EXAMPLES

The present technology is further illustrated by the following examples, which should not be construed as limiting in any way. The Examples described below illustrate methods for producing and manufacturing IMOs that pertain to the present technology. In the Examples, an *Aspergillus niger* invertase was employed to produce IMOs from a maltose-based (corn syrup) substrate. It is understood that an invertase derived from another source, e.g., from *Aspergillus oryzae*, could also be employed. Hydrolysis and transglycosylation of maltose is essential for IMO production. Conventional IMO production is performed via a two-step saccharification process. The two reactions include separate or sequential maltogenic and transglucosidic reactions. Using the conventional method, β-amylase was first reacted with a liquefaction syrup to produce maltose, and transglucosidase, i.e., TG, was subsequently added to produce IMOs. However, by employing the improved simultaneous method as further described below, it is now possible to concomitantly add invertase, in the presence of β-amylase, to a liquefaction syrup for IMO production. Accordingly, the examples below demonstrate that an invertase from *Aspergillus niger* has the functional capability of producing IMOs from a maltose substrate via a previously undiscovered transglucosidic mechanism.

Example 1

Conventional Method for IMO Production

A starch slurry was prepared by adding 1 kg of corn starch and 1.5 kg of water into a vessel for a final concentration of 19-22° Be. The liquefying enzyme, 0.04-0.05% (w/w/ds) of heat stable α-amylase from *Bacillus lichemiformis* (Novo Nordsik, Denmark), was added to the slurry at 105° C. for 10 min at a pH of 5.8-6.1. The liquefied syrup was subsequently subjected to a second liquefaction process via passing the syrup through flushing tanks for 2 hours thereby producing a final 10-12 dextrose equivalent ("DE") syrup. The liquefied slurry was then subjected to a first saccharification reaction by adding 0.052% (w/w) β-amylase from barley (Genencor, Rochester, N.Y.), and 0.07% (w/w) pullulanase from *Bacillus lichemiformis* (Amano Pharmaceuticals, Japan), at 60-65° C., at a pH between 5.0-5.5, for 48-72 hours. A second saccharification reaction was performed by adding a 0.1% (w/w) solution of transglucosidase from *Aspergillus niger* (Genencor, Rochester, N.Y.) and reacting the mixture at 55-60° C. for 48-72 hours. Unreacted materials were removed from the saccharified solution by filtration and the saccharified solution was treated with activated carbon to remove color. The saccharified solution was passed over a carbon column charged with granular active carbon at a temperature between 60-75° C. for approximately 30 minutes to 3 hours. Cation, anion, and mixed bed, exchange resins (Samyang Genex, Korea) were employed to chromatographically separate ionic components from the solution at a flow rate of 5-10 $m^3$/hr at 30-50° C. Finally, the IMO syrup was concentrated to about 75° Bx via a MVR evaporator.

Example 2

Simultaneous Method for IMO Production with Invertase

A starch slurry was prepared by adding 1 kg of corn starch and 1.5 kg of water into a vessel for a final concentration of 19-22° Be. The liquefying enzyme, 0.04-0.05% (w/w/ds) of heat stable α-amylase (as listed in Example 1), was added to the slurry at 100-108° C. for 2-2.5 hours at a pH of 5.8-6.1. The liquefied slurry was subsequently subjected to a single saccharification step. Here, 0.052% (w/w) β-amylase from barley (Genencor, Rochester, N.Y.), 0.07% (w/w) pullulanase from *Bacillus lichemiformis* (Amano Pharmaceuticals, Japan), and 0.16% (w/w) *Aspergillus niger* invertase were added to the liquefied slurry for a final concentration of 35-40° Bx at pH 5.0-5.5. The saccharification mixture was reacted at 60-65° C. for 48-72 hours. Unreacted materials were removed from the saccharified solution by filtration. The saccharified solution was treated with activated carbon to remove color as described above in Example 1. Ion exchange resins were utilized to separate ionic components from the solution as described above in Example 1. Finally, the IMO syrup was concentrated to 75° Bx via a MVR evaporator. See FIG. 1.

Example 3

Comparison of the Conventional and Simultaneous Methods for Production

Figure 2:
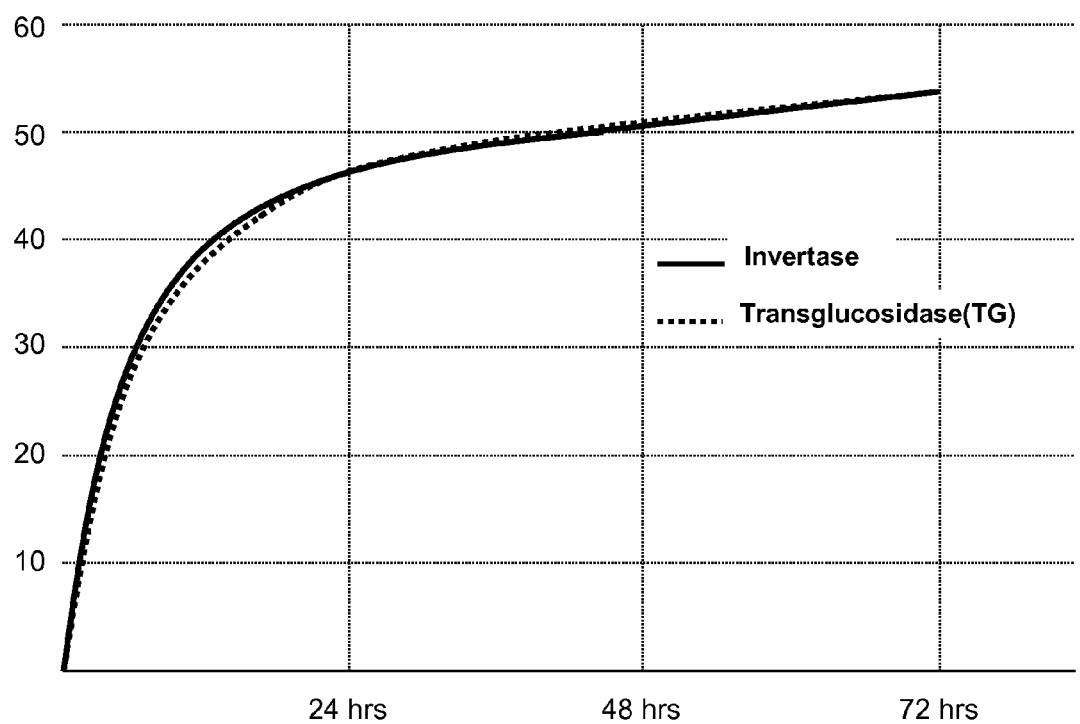
FIG. 2 is a graph depicting the change in IMO content during the conventional and simultaneous saccharification reactions.

This example compared the change in IMO content during saccharification. For the conventional and simultaneous methods, the reactions were performed as described above. FIG. 2 demonstrates that the dry base percentage (DB %) of oligosaccharides are identical for the conventional and simultaneous methods. The abscissa delineates the time-length in hours for a complete saccharification reaction, and the DB % is represented on the ordinate. See FIG. 2.

Example 4

Comparison of the Sugar Profiles for the Conventional and Simultaneous Methods

In separate experiments, the IMO sugar profiles were compared for the conventional and simultaneous methods. As demonstrated by Table 1, the total IMO production profiles were identical for the conventional and simultaneous methods. As shown in Table 1, the total IMO production includes: isomaltose; branched glucose; DP3 glucose; panose; isomaltotriose; isomaltotetraose; and isomaltoheptaose.

TABLE 1

Sugar Profiles for the Conventional and Simultaneous Method

| Sugar profile (DB %) | Conventional | Simultaneous |
| --- | --- | --- |
| Glucose | 18~20 | 20~22 |
| Maltose | 12~15 | 10~13 |
| Isomaltose | 4~6 | 5~7 |
| Branched glucose, DP3 glucose | 2~4 | 5~7 |
| Maltotriose | 3~5 | 3~5 |
| Panose | 20~22 | 18~20 |
| Isomaltotriose | 0~2 | 0~2 |
| Isomaltotetraose~Isomaltoheptaose | 18~20 | 22~24 |
| Maltooctaose | 5~10 | 5~10 |
| Total Isomaltooligosaccharides | 50~53 | 50~53 |

Accordingly, as demonstrated by the foregoing Examples, an invertase isolated from *Aspergillus niger* possesses transglucosidase activity. This novel invertase contains the unexpected feature of having the ability to contact and react with a maltose substrate. This novel invertase surprisingly and unexpectedly improves the conventional method for producing IMOs by catalyzing a simultaneous, single step, saccharification reaction. This new method will reduce IMO manufacturing costs by decreasing the time and energy required to produce IMOs.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language including, but not limited to, e.g., "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for making an isomaltooligosaccharide composition comprising the steps of:
    (a) contacting a starch slurry with a liquefaction enzyme at a temperature of about 100° C. to about 108° C. and pH of about 5-7 for 60-210 min; and
    (b) contacting the product of step (a) with a maltogenic enzyme and an invertase at a temperature above 10° C. and below 85° C. and at a pH above 2 and below 10, wherein the maltogenic enzyme and the invertase are simultaneously contacted with the product of step (a) to produce isomaltooligosaccharides.

2. The method of claim 1, wherein the slurry comprises 15% to 45% by weight of starch.

3. The method of claim 1, wherein the invertase is at least 0.0009% by weight of all reactants of the step (b).

4. The method of claim 1, wherein the invertase is less than 2% by weight of all reactants of the step (b).

5. The method of claim 1, wherein the isomaltooligosaccharides are selected from the group consisting of isomaltose, branched glucose, DP3 glucose, DP3 glucose having alpha-1,4 and/or alpha-1,6 linkages, panose, isomaltotriose, isomaltotetraose, isomaltopentaose, isomaltohexaose, and isomaltoheptose, or any combination thereof.

6. The method of claim 5, wherein at least 10% w/w of the produced isomaltooligosaccharides is panose.

7. The method of claim 1, further comprising purifying the isomaltooligosaccharide composition.

8. The method of claim 1, wherein the liquefaction enzyme is an alpha-amylase.

9. The method of claim 1, wherein the maltogenic enzyme is a beta-amylase or a fungal alpha-amylase.

10. The method of claim 1, wherein the invertase has transglucosidase activity.

11. The method of claim 1, wherein the invertase is an *Aspergillus* invertase.

12. The method of claim 11, wherein the *Aspergillus* invertase is an *Aspergillus niger* invertase or an *Aspergillus oryzae* invertase.

13. The method of claim 1, wherein the slurry is formed from one or more starches and liquid.

14. The method of claim 1, further comprising adding pullulanase to step (b).

15. The method of claim 1, wherein the starch slurry comprises one or more substrates selected from the group consisting of corn starch, rice starch, wheat starch, tapioca, potato starch, sweet potato starch, sago starch, barley starch, heat/acid treated starch, pearl starch, waxy corn starch, sorghum starch, high amylose corn starch, liquid dextrose, and combinations thereof.

16. The method of claim 15, wherein the starch slurry comprises corn starch.

\* \* \* \* \*